United States Patent [19]
Fisher

[11] Patent Number: 6,053,876
[45] Date of Patent: Apr. 25, 2000

[54] APPARATUS AND METHOD FOR MARKING NON-PALPABLE LESIONS

[76] Inventor: John Fisher, 603 Ponce de Leon, Bellair, Fla. 33756

[21] Appl. No.: 09/328,548

[22] Filed: Jun. 9, 1999

[51] Int. Cl.⁷ ..................................................... A61B 5/00
[52] U.S. Cl. ........................................... 600/562; 600/570
[58] Field of Search .................... 600/562, 564, 600/570

[56] References Cited

U.S. PATENT DOCUMENTS

| | | | |
|---|---|---|---|
| 3,831,584 | 8/1974 | Bronny et al. | 600/570 |
| 4,338,952 | 7/1982 | Augros | 600/570 |
| 4,796,329 | 1/1989 | Simon | 600/562 |
| 5,092,345 | 3/1992 | Sakita | 600/570 |

*Primary Examiner*—Cary O'Connor
*Assistant Examiner*—Pamela Wingood
*Attorney, Agent, or Firm*—Smith and Hopen, P.A.; Ronald E. Smith

[57] ABSTRACT

A surgical tool forms a collapsible cage that surrounds a lesion or a tumor in a breast or soft tissue so that removal of all encaged tissue ensures the removal of the tumor or lesion. The collapsibility of the cage enables it to be closed and repositioned if needed. A leading tube and a trailing tube are interconnected by a plurality of circumferentially spaced apart members that are jointed at their respective mid-lengths. The respective leading ends of the jointed members are hingedly connected to a trailing end of the leading tube and the respective trailing ends of the jointed members are hingedly connected to the leading end of the trailing tube. The leading and trailing tubes slidingly receive a hollow needle and the leading tube is secured to the hollow needle at its distal end so that the leading tube cannot slide with respect to the hollow needle. Sliding the trailing tube toward the leading tube causes the jointed members to bend at their respective mid-lengths and to displace radially outwardly at their respective mid-joints, relative to a longitudinal axis of the leading and trailing tubes. A lesion is encaged by the jointed wires and a surgeon removes all encaged tissue to ensure removal of the lesion. If the lesion is not fully encaged, the trailing tube is retracted to return the jointed members to a substantially straight configuration so that the hollow needle can be withdrawn from the breast and an additional attempt to properly position it can be made.

5 Claims, 3 Drawing Sheets

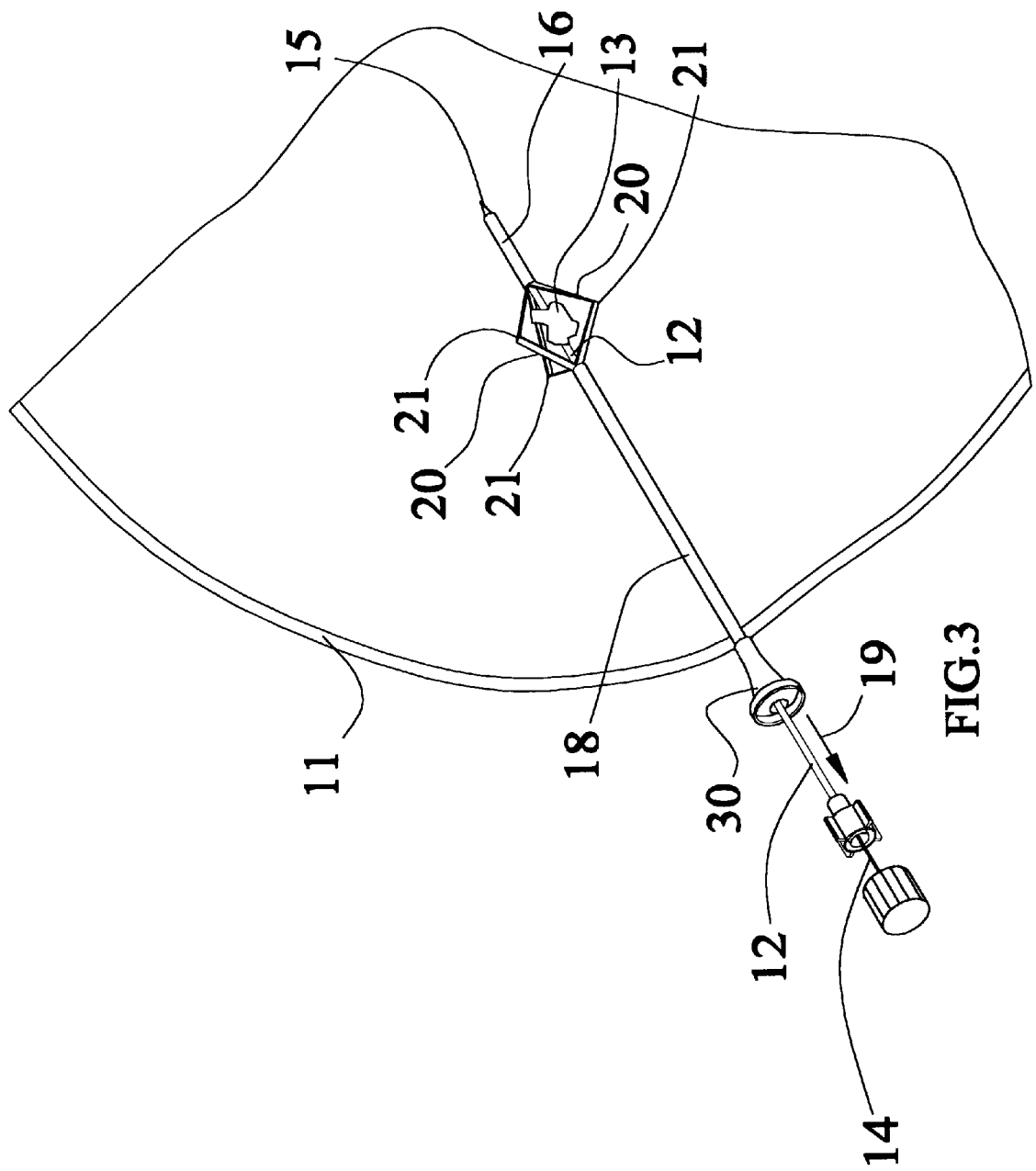

APPARATUS AND METHOD FOR MARKING NON-PALPABLE LESIONS

BACKGROUND OF THE INVENTION

1. Field of the Invention

This invention relates, generally, to surgical tools and methods for their use. More particularly, it relates to a needle apparatus and a method for marking the location of a lesion or a tumor in a breast or soft tissue.

2. Description of the Prior Art

Mammography enables the detection of very small lesions or tumors in a breast, even if the individual is experiencing no symptoms. However, if the lesion or tumor is non-palpable, it can be difficult for the surgeon to locate it and remove it through surgery.

A lesion may be non-palpable because it is very small. It may even be relatively large, but still non-palpable because it resides in a large breast or in a smaller breast but deep within the tissue mass.

In one prior art procedure, developed by Kopans, a hypodermic needle is placed into the breast so that the tip of the needle is near the lesion.

After the needle tip is positioned near the lesion, a stainless steel wire having a thin hooked distal end is introduced into the proximal end of the hollow bore of the needle and pushed toward the lesion until the thin hooked distal end of the wire protrudes from the distal end of the needle. The wire is thickened near its distal end, purportedly to make the wire palpable. The hook engages the breast tissue in the vicinity of the lesion and holds the wire in place. Additional mammograms are then taken to verify the respective positions of the needle, the wire, and the hook. If the position of the apparatus is satisfactory, the needle is withdrawn from the breast, leaving the stainless steel wire unmoved because it is not connected to the needle. The surgeon then follows the wire to the lesion and removes the tissue in the vicinity of the hook.

The breast, however, must be compressed during the taking of a mammogram. The compression often causes the needle to migrate during mammagraphic filming; this causes uncertainty about the location of the hook.

Moreover, if the position of the hook is determined to be unsatisfactory, i.e., too far from the lesion, the hook cannot be extracted easily so that another attempt can be made to position it closer to the lesion. Forceful retraction of the hook can damage breast tissue. The hook might even break off and be lost in the tissue mass.

What is needed, then, is an improved method for marking the position of a breast lesion or tumor. The new method should facilitate additional attempts to better position the needle if the initial needle insertion proves to be unsatisfactory. There should be no tissue damage caused by withdrawing a wire hook and there should be no broken hooks left within a breast.

However, it was not obvious to those of ordinary skill in this art how the needed improvements could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention.

The novel method for marking the location of a lesion or tumor in a breast includes the step of providing a needle having an internal bore into which a stylet having a pointed end is received.

A leading tube and a trailing tube that share a common internal diameter slightly greater than the external diameter of the needle slidingly receive the needle and are interconnected to one another by a plurality of circumferentially spaced apart jointed members.

The leading tube is secured to the needle so that it can not slide with respect to the needle.

The jointed members are hingedly connected at their respective leading ends to a trailing end of the leading tube and are hingedly connected at their respective trailing ends to a leading end of the trailing tube. The jointed members are hingedly jointed at their respective midpoints so that they are in substantially parallel relation to one another when the leading and trailing tubes are positioned a maximum longitudinal distance from one another. Sliding displacement of the trailing tube toward the stationary leading tube causes the respective midpoints to collectively diverge from one another in a radially outwardly direction.

If the needle is not well positioned, the trailing tube is simply retracted with respect to the leading tube and such retraction flattens the jointed members against the external surface of the needle so that the needle can be withdrawn and reinserted.

When the trailing tube is displaced toward the leading tube, in a proximal-to-distal direction, the jointed members collectively diverge from one another in a radially outward direction at their respective jointed midpoints to form a cage means that surrounds the lesion. Removal of all breast tissue encaged by the jointed members includes removal of the lesion or tumor.

It is a primary object of this invention to advance the art of marking the location of non-palpable lesions or tumors in a breast.

A more specific object is to provide a method for marking lesions or tumors that enables a physician to make multiple attempts, if needed, to place a marker needle near a lesion without causing undue damage to breast tissue.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 3 is a perspective view depicting the second step.

DETAILED DESCRIPTION OF THE PREFERRED EMBODIMENT

Figure 1:
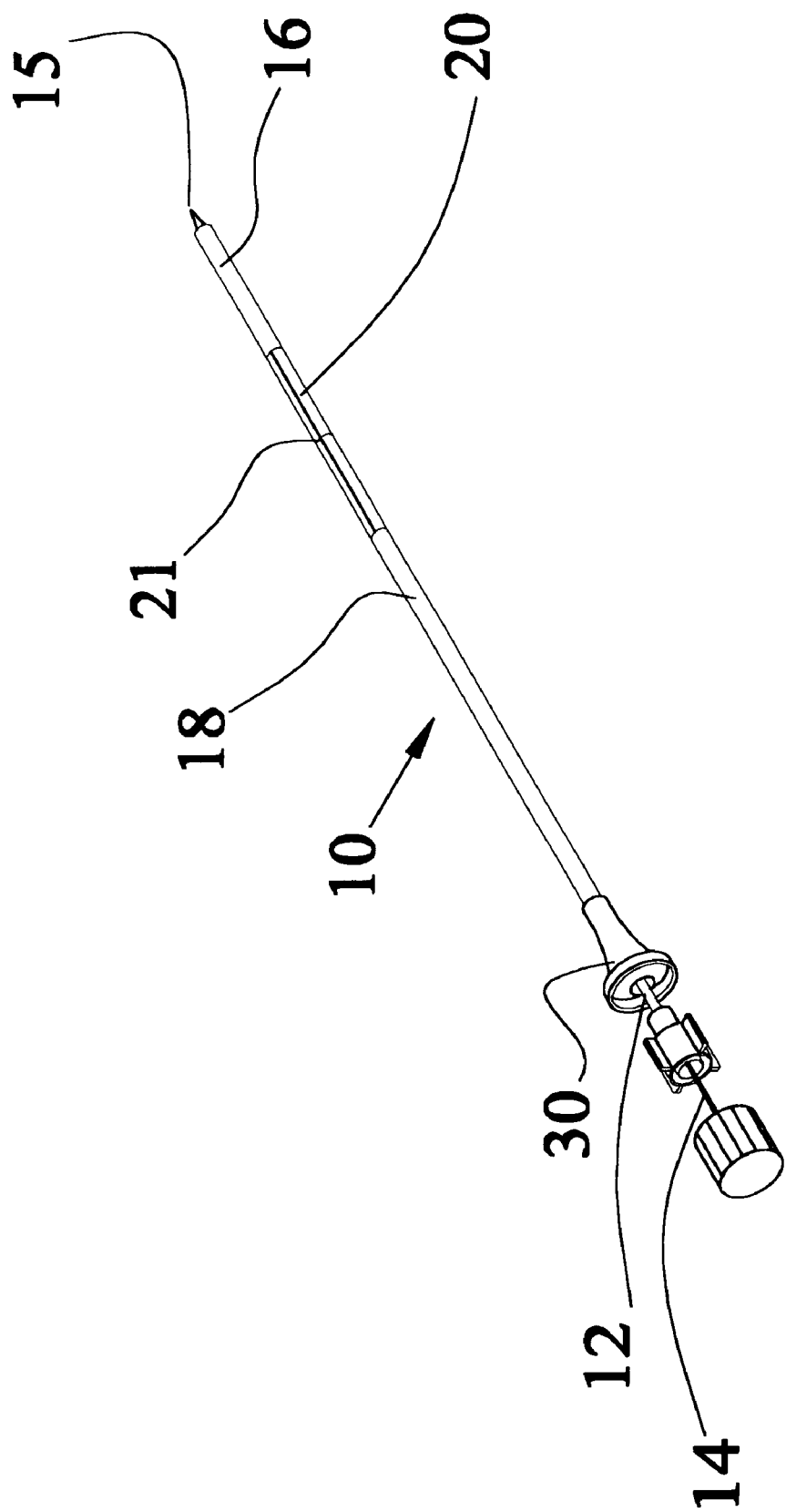
FIG. 1 is a perspective view depicting the novel tool.

FIG. 1 depicts the novel structure 10. A hollow bore needle 12 slideably receives a stylet 14 having a pointed distal end 15. Stylet 14 has a predetermined length that exceeds the length of needle 12.

Needle 12 is received within the hollow bore of a leading tube 16 and a trailing tube 18 that are interconnected to one another by a plurality of jointed members 20 that are made of the same resilient and flexible material as tubes 16 and 18.

Leading tube 16 is secured by suitable means, such as by an adhesive, to needle 12 so that leading tube 16 is not slideably displaceable relative to needle 12.

Trailing tube 18 is not adhered or otherwise affixed to needle 12 and therefore said trailing tube may be displaced in sliding relation along the extent of needle 12.

Figure 2:
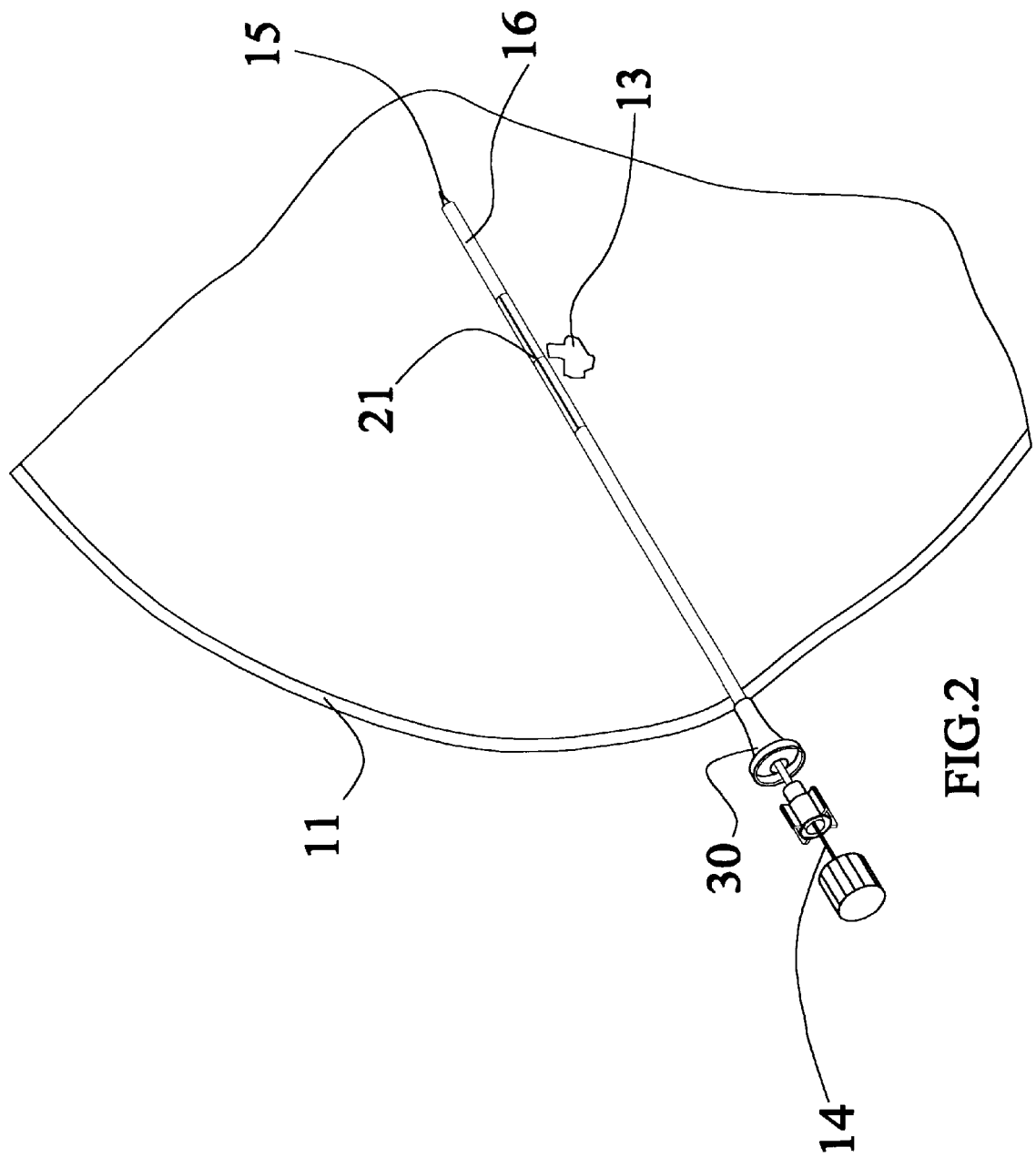
FIG. 2 is a perspective view depicting the first step of the novel method.

Jointed members 20 are disposed in substantially parallel relation to one another when leading and trailing tubes 16 and 18 are at their maximum longitudinal spacing with respect to one another, as indicated in FIGS. 1 and 2. Said jointed members are not secured to needle 12.

The respective leading or distal ends of jointed members 20 are hingedly secured by suitable means to the trailing or proximal end of leading tube 16 and the respective proximal ends of jointed members 20 are hingedly mounted by suitable means to the leading or distal end of trailing tube 18. The suitable means in each case may be a living hinge.

A similar living hinge, collectively denoted 21, is formed mid-length of each jointed member and is structured to permit radially outward displacement only. It follows that, as aforesaid, jointed members 20 are substantially parallel to one another when leading and trailing tubes 16 and 18 are at their maximum longitudinal spacing from one another. However, when the longitudinal spacing between the leading and trailing tubes is reduced, by sliding trailing tube 18 in a proximal-to-distal direction toward stationary leading tube 16, jointed members 20 bend at their respective joints 21.

Specifically, as depicted in FIG. 3, joints 21 displace radially outwardly with respect to a common longitudinal axis of leading tube 16 and trailing tube 18 as the distance between said tubes is reduced. Thus, when the novel procedure is performed, leading tube 16 is stationary with respect to needle 12 and trailing tube 18 is moved toward it, thereby causing the radial displacement of jointed members 20 at their respective midpoints.

As indicated in FIG. 2, needle 12 is first advanced into a breast mass 11 or other soft tissue past lesion 13 by a distance selected by the physician.

In FIG. 3, the physician has advanced trailing tube 18 toward leading tube 16, thereby causing jointed members 20 to begin to displace radially away from one another with respect to needle 12. Note that lesion 13 is now encaged by said jointed members.

Locking device 30 may be used to advance trailing tube 18 by pushing against its trailing end. Suitable locking means are included to secure locking device 30 on needle 12 to prevent distal-to-proximal displacement of trailing tube 20 after it has been advanced in a proximal-to-distal direction. The locking means, when locked, prevents distal-to-proximal travel of trailing tube 18 and thus prevents return of the jointed members 20 to their FIG. 2 position. The tissue encaged by jointed members 20 is then ready for surgical removal. In this way, removal of lesion 13 is assured.

If it is discovered upon full expansion of jointed members 20 that lesion 13 is not fully encaged by the jointed members, and that re-positioning of the assembly is needed, trailing tube 18 is retracted in the direction indicated by directional arrow 19 in FIG. 3 and jointed members 20 are returned to their substantially parallel relation to one another. This enables retraction of the assembly so that needle 12 may be reinserted into the breast or soft tissue a second time to better position it. Since jointed members 20 are fully retractable after expansion, multiple re-positioning of needle 12 is possible without unduly injuring tissue.

Jointed members 20 are preferably made of a polymer or an alloy with shape memory.

This invention represents a major breakthrough in the art of breast lesion or tumor location marking. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for marking the location of a lesion or tumor in a breast, comprising the steps of:

providing a hollow needle having a bore of preselected diameter;

providing a leading tube and a trailing tube that share a common internal diameter slightly greater than an external diameter of said hollow needle;

interconnecting said leading tube and trailing tube with a plurality of circumferentially spaced apart jointed members that are hingedly connected at their respective leading ends to a trailing end of said leading tube, hingedly connected at their respective trailing ends to a leading end of said trailing tube, and hingedly jointed at their respective mid-points so that said jointed members are in substantially parallel relation to one another when said leading and trailing tubes are positioned a maximum longitudinal distance from one another and so that sliding displacement of said trailing tube toward said leading tube causes said respective mid-points to collectively diverge from one another in a radially outwardly direction;

sliding said trailing tube toward said leading tube in a proximal-to-distal direction so that said jointed members collectively diverge from one another in said radially outward direction at said respective jointed midpoints; and removing breast tissue encaged by said jointed members to remove said lesion or tumor.

2. The method of claim 1, further comprising the step of providing a locking means that engages a trailing end of said trailing tube to hold said trailing tube against distal-to-proximal movement after said trailing tube has been displaced in said proximal-to-distal movement toward said leading tube.

3. An apparatus for encaging a lesion or tumor in a breast, comprising:

a hollow needle having a predetermined external diameter and an internal bore;

a leading tube and a trailing tube that have a common internal diameter slightly greater than said external diameter of said hollow needle;

a plurality of circumferentially spaced apart jointed members for interconnecting said leading and trailing tubes to one another;

said jointed members having respective leading ends hingedly connected to a trailing end of said leading tube;

said jointed members having respective trailing ends hingedly connected to a leading end of said trailing tube;

each of said jointed members having a radially outwardly bending joint formed mid-length thereof so that convergence of said leading and trailing tubes causes said jointed members to expand radially outwardly with respect to a common axis of said leading and trailing tubes.

4. The apparatus of claim 3, further comprising an elongate stylet slideably received within said internal bore, said elongate stylet having a predetermined length that exceeds that of said hollow needle so that a pointed distal end of said stylet protrudes from a distal end of said elongate needle when said stylet is fully received within said internal bore.

5. The apparatus of claim 4, further comprising a locking means adapted to engage a proximal end of said trailing tube to hold said trailing tube against distal-to-proximal movement after said trailing tube has been displaced in a proximal-to-distal direction toward said leading tube.

* * * * *